(12) United States Patent
Yamagata et al.

(10) Patent No.: US 11,109,810 B2
(45) Date of Patent: Sep. 7, 2021

(54) INFORMATION DISPLAY DEVICE, BIOLOGICAL SIGNAL MEASUREMENT SYSTEM, AND COMPUTER PROGRAM PRODUCT

(71) Applicants: Hideaki Yamagata, Kanagawa (JP); Noriyuki Tomita, Ishikawa (JP)

(72) Inventors: Hideaki Yamagata, Kanagawa (JP); Noriyuki Tomita, Ishikawa (JP)

(73) Assignee: RICOH COMPANY, LTD., Tokyo (JP)

( * ) Notice: Subject to any disclaimer, the term of this patent is extended or adjusted under 35 U.S.C. 154(b) by 383 days.

(21) Appl. No.: 16/284,015

(22) Filed: Feb. 25, 2019

(65) Prior Publication Data
US 2019/0282176 A1 Sep. 19, 2019

(30) Foreign Application Priority Data
Mar. 15, 2018 (JP) .............................. JP2018-047450

(51) Int. Cl.
*A61B 5/00* (2006.01)
*G06F 17/14* (2006.01)
*A61B 5/245* (2021.01)

(52) U.S. Cl.
CPC ............ *A61B 5/7235* (2013.01); *A61B 5/245* (2021.01); *G06F 17/142* (2013.01)

(58) Field of Classification Search
CPC ...... A61B 5/7235; A61B 5/245; G06F 17/142

USPC .......................................... 600/409
See application file for complete search history.

(56) References Cited

U.S. PATENT DOCUMENTS

2014/0195202 A1* 7/2014 Ishiguro ............... A61B 5/7235
    702/199
2014/0343427 A1* 11/2014 Fukunaga ............. A61B 5/363
    600/440

FOREIGN PATENT DOCUMENTS

| JP | 2009-195571 | 9/2009 |
| JP | 2012-170701 | 9/2012 |
| JP | 2018-153469 | 10/2018 |
| JP | 2018-153614 | 10/2018 |

* cited by examiner

*Primary Examiner* — Allen C Wong
(74) *Attorney, Agent, or Firm* — Harness, Dickey & Pierce, P.L.C.

(57) ABSTRACT

An information display device includes a component extraction unit, a sorting unit, and a noise component selection unit. The component extraction unit is configured to perform a principal component analysis or an independent component analysis to extract desired components from a plurality of signal waveforms based on detected biological signals. The sorting unit is configured to sort a plurality of extracted results obtained by the component extraction unit in descending order of periodicity and display the sorted results. The noise component selection unit is configured to receive selection of one extracted result as a noise component from the extracted results obtained by the component extraction unit.

6 Claims, 21 Drawing Sheets

FIG.7

Annotation List

☑ Show Markup on wave ——————— 180a

| No. | | File | Time | Event | MEMO | Cluster |
|---|---|---|---|---|---|---|
| ■☐ | | 001 | 00:09:30 | 🔥 | normal spike | B |
| ■☐ | | 001 | 00:05:00 | 🔥 | strong spike | A |
| ■☐ | | 000 | 00:00:00 | 🔥 | Dr.memo | A |

Exit Measurement

180

INFORMATION DISPLAY DEVICE, BIOLOGICAL SIGNAL MEASUREMENT SYSTEM, AND COMPUTER PROGRAM PRODUCT

CROSS-REFERENCE TO RELATED APPLICATIONS

The present application claims priority under 35 U.S.C. § 119 to Japanese Patent Application No. 2018-047450, filed on Mar. 15, 2018. The contents of which are incorporated herein by reference in their entirety.

BACKGROUND OF THE INVENTION

1. Field of the Invention

The present invention relates to an information display device, a biological signal measurement system, and a computer program product.

2. Description of the Related Art

A magnetoencephalograph (MEG) is a device that measures a weak magnetic field generated by neural activities in the brain to examine brain functions.

When the magnetic, field is measured using the magnetoencephalograph, biologically dependent noise, such as a magnetic field generated from the heart, is mixed in, in some cases. Accordingly, several technologies are disclosed to remove the noise mixed in the measured brain magnetic field signals.

Japanese Unexamined Patent Application Publication No. 2009-195571 discloses a technology that detects time of occurrence of the noise by analyzing a magnetic field waveform using a dedicated device for measuring a cardiac magnetic field, and subtracts the noise signals from the original magnetic field signals to remove the noise mixed in the brain magnetic field signals.

However, the conventional technology uses the waveform of the cardiac magnetic field obtained from the dedicated device for measuring the cardiac magnetic field. Therefore, when the technology is applied to the magnetic field signals obtained by the magnetoencephalograph, it is difficult to clearly distinguish the waveform of the magnetic field generated from the heart that is mixed in as the noise. In addition, the conventional technology requires an external device for synchronizing with the occurrence of the noise, and thus, the device configuration is complicated.

SUMMARY OF THE INVENTION

According to one aspect of the present invention, an information display device includes a component extraction unit, a sorting unit, and a noise component selection unit. The component extraction unit is configured to perform a principal component analysis or an independent component analysis to extract desired components from a plurality of signal waveforms based on detected biological signals. The sorting unit is configured to sort a plurality of extracted results obtained by the component extraction unit in descending order of periodicity and display the sorted results. The noise component selection unit is configured to receive selection of one extracted result as a noise component from the extracted results obtained by the component extraction unit.

BRIEF DESCRIPTION OF THE DRAWINGS

FIG. 7 is an enlarged view illustrating an annotation list;

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENT

Figure 1:
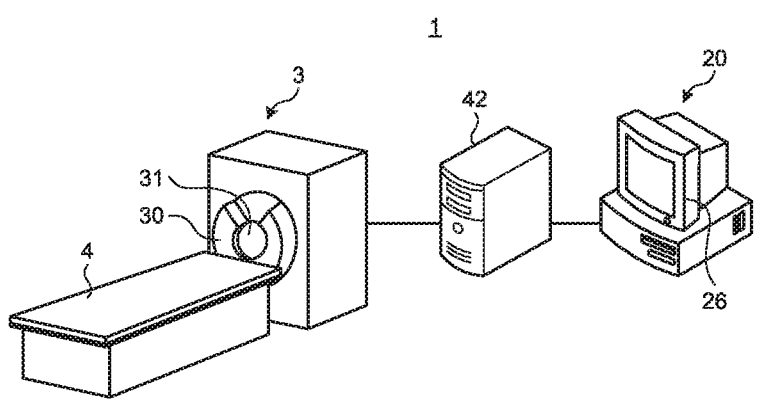
FIG. 1 is a schematic diagram of a biological signal measurement system according to an embodiment of the present invention.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to facilitate the detection of the noise components superimposed on the biological signals.

FIG. 1 is a schematic diagram of a biological signal measurement system 1 according to an embodiment of the present invention. The biological signal measurement system 1 measures and displays a plurality of types of biological signals including, for example, magnetoencephalographic {MEG} signals and electroencephalographic {EEG} signals.

As illustrated in FIG. 1, the biological signal measurement system 1 includes a measurement device 3, a measurement table 4, a data recording server 42, and an information display device 20. The information display device 20 includes a monitor display 26 that displays signal information obtained by measurement and analysis results. The present embodiment provides the data recording server 42 and the information display device 20 in a separate manner, but at least a part of the data recording server 42 may be incorporated in the information display device 20.

A measurement subject serving as a measurement target lies on his or her back on the measurement table 4 with electrodes (or sensors) for EEG measurement attached to the head, and places the head in a recess 31 of a dewar 30 of the measurement device 3. The dewar 30 is a container under a cryogenic environment using liquid helium, and many magnetic sensors for the MEG measurement are disposed in the recess 31 of the dewar 30. The measurement device 3 collects the EEG signals from the electrodes and the MEG signals from the magnetic sensors. The measurement device 3 outputs the collected biological signals to the data recording server 42.

Although, in general, the dewar 30 incorporating the magnetic, sensors and the measurement table 4 are disposed in a magnetic shielding room, the magnetic shielding room is not illustrated for convenience of illustration.

The data recording server 42 records data including, for example, the biological signals output from the measurement device 3.

Figure 2:
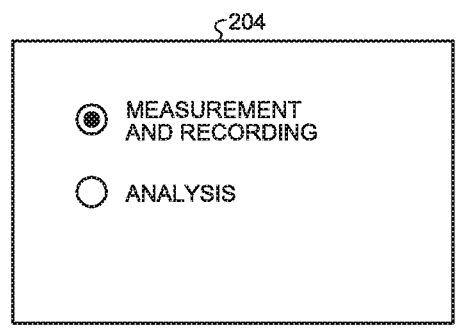
FIG. 2 is a front view illustrating an example of a starting screen.

The information display device 20 reads the data recorded in the data recording server 42, displays the data on the monitor display 26, and analyzes the data. The information display device 20 displays waveforms of the MEG signals obtained from the magnetic sensors and waveforms of the EEG signals obtained from the electrodes in synchronization with each other on the same time axis. The EEG signals represent electrical activities of neurons (flow of ionic charges occurring at dendrites of neurons during synaptic transmission) as voltage values between the electrodes. The MEG signals represent small variations of the magnetic field caused by electrical activities of the brain. The brain magnetic field is detected by highly sensitive superconducting quantum interference device (SQUID) sensors. FIG. 2 is a front view illustrating an example of a start screen 204 displayed on the monitor display 26 of the information display device 20. As illustrated in FIG. 2, selection boxes for "Measurement and Recording" and "Analysis" are displayed on the start screen 204 displayed on the monitor display 26 of the information display device 20. In the case of either the EEG measurement or the MEG measurement or both, the measurement and recording of the date and the analysis of the data are often performed by different persons. For example, if the box for "Measurement and Recording" of the start screen 204 is selected by a measurement engineer (measurer), the measurement device 3 sequentially stores the measured data in the data recording server 42. The information display device 20 reads the data stored in the data recording server 42, and displays the data on the monitor display 26. After the measurement and recording are finished, if the selection box for "Analysis" of the start screen 204 is selected by an analyst such as a medical doctor, the information display device 20 reads and analyzes the measured data stored in the data recording server 42.

Operations During Measurement and Recording

First, operations of the information display device 20 during the measurement and recording will be described.

Figure 3:
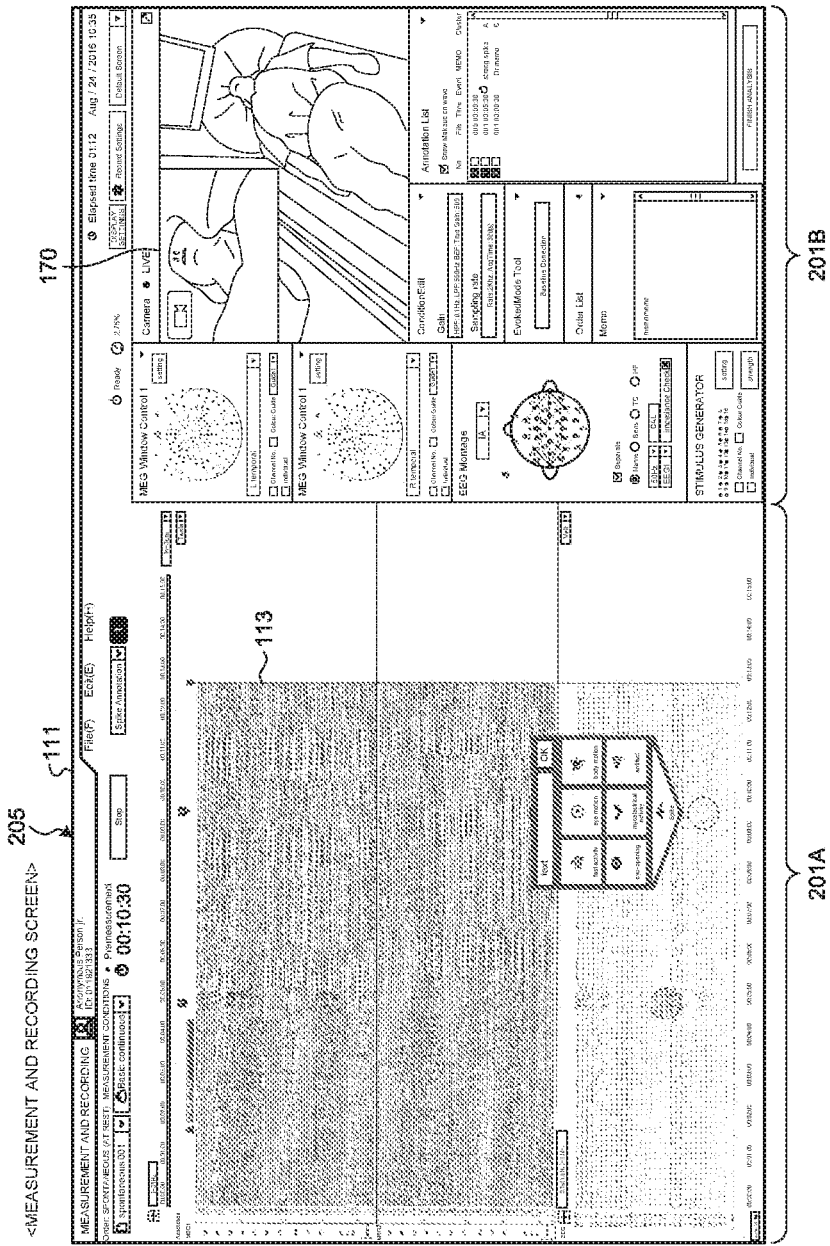
FIG. 3 is a front view illustrating an example of a measurement and recording screen.

FIG. 3 is a front view illustrating an example of a measurement and recording screen 205 displayed during the measurement and recording on the monitor display 26 of the information display device 20. As illustrated in FIG. 3, a tab 111 on the screen displays that the measurement and recording screen 205 is a "Measurement and Recording" screen. The measurement and recording screen 205 includes an area 201A that displays measured signal waveforms and an area 201B that displays monitor information other than the signal waveforms. The area 201A that displays the signal waveforms is disposed on the left, side of the screen as viewed from the measurer, and the area 201B that displays the monitor information other than the signal waveforms is disposed on the right side of the screen as viewed from the measurer. The measurement and recording screen 205 allows an efficient movement of the line of sight of the measurer in accordance with the movement of the waveforms (displayed from the left side toward the right side of the screen) detected and displayed in real time, and an efficient movement of a mouse from the left-side area 201A to the right-side area 201B of the screen, and thus increases operating efficiency.

The measurement and recording screen 205 displays a monitor window 170 for chocking the state of the measurement subject during the measurement in the area 201B of the display screen. The measurement and recording screen 205 displays a live video of the measurement subject while being measured, and can thereby increase the reliability of checking and judgment of the signal waveforms, as will be described later.

In the measurement and recording screen 205 illustrated in FIG. 3, a case is illustrated where the entire measurement and recording screen 205 is displayed in the display screen on one monitor display 26. However, the left-side area 201A and the right-side area 201B may be separately displayed on two or more monitor displays.

Figure 4:
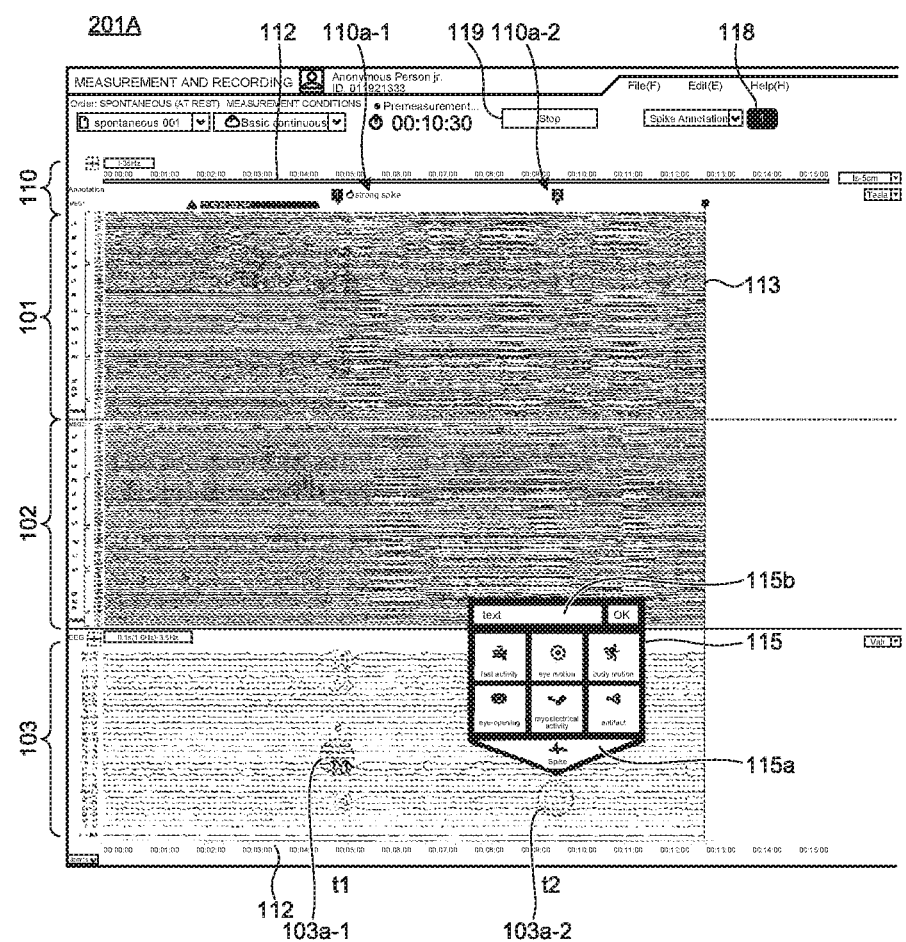
FIG. 4 is an enlarged view of a left-side area of the measurement and recording screen.

FIG. 4 is an enlarged view of the left-side area 201A of the measurement and recording screen 205. As illustrated in FIG. 4, the area 201A includes a first display portion 110 that displays time information on the signal detection in the horizontal direction (first direction) of the screen and second display portions 101 to 103 that display a plurality of signal waveforms based on the signal detection arranged in parallel in the vertical direction (second direction) of the screen.

In the example illustrated in FIG. 4, the time information displayed in the first display portion 110 is a timeline including time indications noted along a time axis 112. However, the time information may only be the band-like axis without displaying the time (digits), or may only display the time (digits) without providing the axis. The timeline may also be displayed by displaying the time axis 112 below the display portion 103 in addition to the display portion 110 on the upper side of the screen.

The area 201A of the measurement and recording screen 205 displays a plurality of signal waveforms acquired from sensors of the same type, or waveforms of a plurality of types of signals acquired from a group of a plurality of types of sensors, in synchronization with each other on the same time axis. For example, the display portion 101 displays waveforms of a plurality of MEG signals obtained from the right side of the head of the measurement subject, and the display portion 102 displays waveforms of a plurality of MEG signals obtained from the left side of the head of the measurement subject, in parallel with each other. The display portion 103 displays waveforms of a plurality of EEG signals in parallel with each other. The EEG signal waveforms are voltage signals measured between the electrodes. Each of the signal waveforms is displayed in association with the identification number or the channel number of a sensor from which the signal has been acquired.

After the measurement has started and the measurement information has been collected from the sensors, the information display device 20 displays the signal waveforms from left ends of the respective display portions 101 to 103 of the area 201A toward the right direction as time passes. A line 113 on the measurement and recording screen 205 indicates time of the measurement (current time), and moves from the left toward the right of the screen. Once the signal waveforms have been displayed to the right end of the area 201A (right end of the time axis 112), the information display device 20 then gradually erases the signal waveforms rightward from the left end of the screen, sequentially displays new signal waveforms rightward from the left of the erased position, and moves the line 113 rightward from the left end. In addition, the information display device 20 displays the lapse of time corresponding to progression of the measurement on the time axis 112 in the display portion 110 in the horizontal direction. The measurement and recording into the data recording server 42 is continued until an end button 119 is pressed.

The information display device 20 receives a mark on the signal waveforms given to a questionable portion or range when the measurer (recorder) has noticed, for example, a noise waveform, a waveform disturbance, or singularity in amplitude on the signal waveforms in the area 201A of the measurement and recording screen 205 during the data recording. The portion or range of the mark can be specified by a pointer operation or a click operation using the mouse. The information display device 20 displays the specified portion (or range) with emphasis on the signal waveforms of the display portions 101 to 103, and displays the specified portion (or range) on a time position or a time range corresponding to the result of the specification along the time axis 112 of the display portion 110. The information display device 20 stores the information on the mark including the display on the time axis 112, together with the signal waveform data. The portion specified in the area 201A of the measurement and recording screen 205 corresponds to a certain time, and the range specified in the area 201A of the measurement and recording screen 205 corresponds to a certain range including a certain time.

In the area 201A of the measurement and recording screen 205 illustrated in FIG. 4, a range including one or more channels is specified in the display portion 103 at time t1, and a time period including time t1 is highlighted with a mark 103a-1. In the area 201A of the measurement and recording screen 205 illustrated in FIG. 4, an annotation 110a-1 indicating the specification result is displayed on a corresponding time position in the display portion 110 associated with the display of the mark 103a-1. In the area 201A of the measurement and recording screen 205 illustrated in FIG. 4, another waveform position or the vicinity thereof is marked in the display portion 103 at time t2, and a mark 103a-2 is highlighted in that position (at time t2) or the vicinity area thereof (at least a time range or any one of a plurality of waveforms is specified). At the same time, in the area 201A of the measurement and recording screen 205 illustrated in FIG. 4, an annotation 110a-2 is displayed on a corresponding time position (time range) in the display portion 110.

The annotation 110a-1 added in the display portion 110 at time t1 includes, as an example, an annotation identification number and information indicating an attribute of a waveform. In this example, an icon and text information "strong spike" indicating the attribute of the waveform are displayed together with an annotation number "1".

As illustrated in FIG. 4, if the measurer specifies the other waveform position or the vicinity area thereof at time t2, the information display device 20 highlights the mark 103a-2 at the specified portion, and in addition, displays an annotation number "2" on a corresponding time position in the display portion 110. Furthermore, the information display device 20 displays a pop-up window 115 for attribute selection at the highlighted portion. The pop-up window 115 includes selection buttons 115a for selecting various attributes and an input box 115b for entering comments and additional information. The selection buttons 115a represent factors of the waveform disturbance including, for example, "fast activity", "eye motion", "body motion", and "spike" as the waveform attributes. The measurer can check the state of the measurement subject, using the monitor window 170 in the area 201B of the screen, and can therefore appropriately select an attribute representing a cause of the waveform disturbance. For example, when a spike occurs in a waveform, the measurer can determine whether the spike is a spike indicating a symptom of epilepsy or a spike caused by a body motion (by, for example, a sneeze) of the measurement subject.

The same operation is also performed at time t1. In FIG. 4, one of the selection buttons 115a "spike" is selected in the pop-up window 115, and "strong spike" is entered in the input box 115b. As a result, the annotation 110a-1 is displayed in the display portion 110. With such a display mode, when the many signal waveforms are displayed in synchronization with each other on the same time axis 112, the measurer can more easily visually specify the portion or range of interest of the signal waveforms, and can easily obtain the basic information on the portion of interest.

A part or the whole of the annotation 110a-1, for example, at least either of the attribute icon and the text annotation may also be displayed near the mark 103a-1 on the signal waveforms in the display portion 103. The addition of the annotation on the signal waveforms may hinder the checking of waveform shapes in some cases. Therefore, selection of display or non-display is preferably allowed when the annotation is displayed on the signal waveforms in the display portions 101 to 103.

The area 201A of the measurement and recording screen 205 includes a counter box 118. The counter box 118 displays a cumulative number of spike annotations. Each time "spike" is selected, the information display device 20 increments a counter value of the counter box 118, and allows the total number of spikes from the start of the recording to the present (line 113) to be grasped at a glance.

Figure 5:
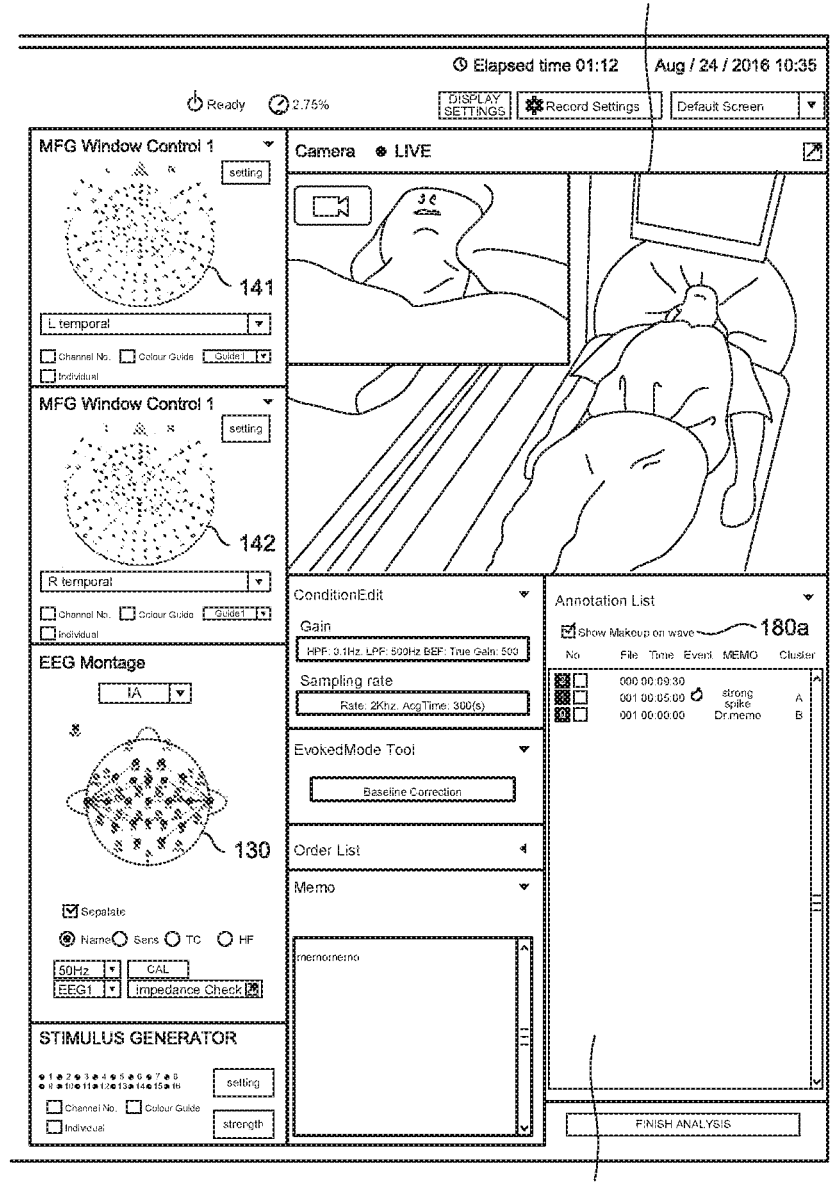
FIG. 5 is an enlarged view of a right-side area of the measurement and recording screen.

FIG. 5 is an enlarged view of the right-side area 201B of the measurement and recording screen 205, and illustrates a state at the same time (time point of the line 113) as that of FIG. 4. The information display device 20 displays the live video of the state of the measurement subject lying on the measurement table 4 with the head placed in the measurement device 3 in the monitor window 170 in the area 201S of the measurement and recording screen 205. The information display device 20 displays distribution diagrams 141, 142, and 130 corresponding to the signal waveforms of the display portions 101, 102, and 103, respectively, and an annotation list 180 in the area 201S of the measurement and recording screen 205.

The annotation list 180 is a list of annotations marked on the signal waveforms of FIG. 4. Each time a position or a range on the signal waveforms is specified in the display portions 101 to 103, corresponding information is sequentially added to the annotation list 180. The addition to the annotation list 180 and display of the annotation list 180 on the measurement and recording screen 205 are performed, for example, in descending order (the newest data is displayed at the frontmost part), but are not limited to this example. The annotation list 180 may be displayed in ascending order, but is displayed such that correspondence relations with annotations displayed along the time axis 112 in the display portion 110 can be understood. Furthermore, the order of the display can be changed, and the sorting can be made for each item.

In the example of the annotation list 130 illustrated in FIG. 5, time information and added annotation information corresponding to the annotation number "1" are listed. The attribute icon representing "spike" and the text "strong spike" are recorded as the annotation information. In the example of the annotation list 180 illustrated in FIG. 5, time information corresponding to the annotation number "2" is listed at the time when the mark 103a-1 is highlighted.

The information display device 20 disposes a display/non-display selection box 180a for selecting the display or non-display of the annotations near the annotation list 180 in the area 201B of the measurement and recording screen 205. If non-display is selected in the selection box 180a, the annotations other than the highlighted mark on the signal waveforms in the display portions 101 to 103 are hidden, but the annotations along the time axis 112 of the display portion 110 keeps being displayed. This operation allows the annotation information to be recognizable without hindering the visibility of the signal waveforms.

Figure 6:
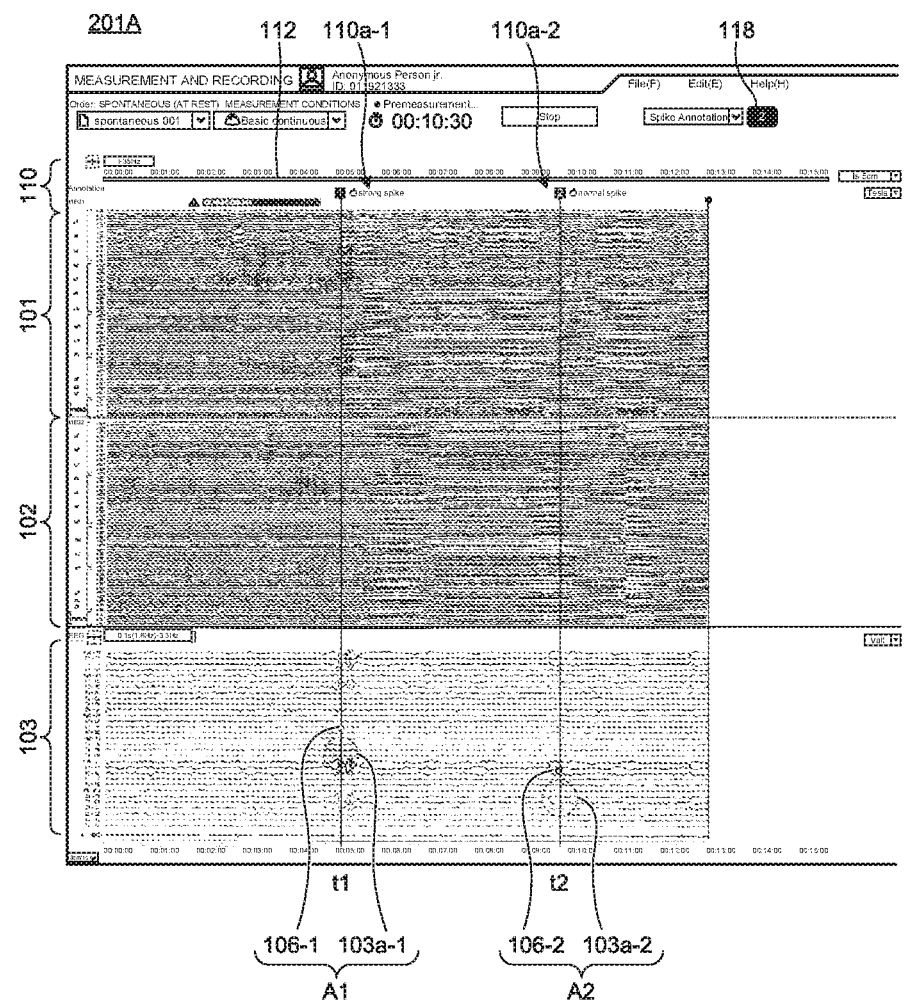
FIG. 6 is an enlarged view of the left-side area of the measurement and recording screen.

FIG. 6 is an enlarged view of the left-side area 201A of the measurement and recording screen 205 immediately after "spike" of the pop-up window 115 is selected and a text "normal spike" is entered at time t2. If an "OK" button is selected in the pop-up window 115 illustrated in FIG. 4, the information display device 20 closes the pop-up window 115, and displays the annotation 110a-2 on the corresponding time position in the display portion 110, as illustrated in FIG. 6. The information display device 20 displays the attribute icon representing "spike" and the text information "normal spike" in association with the annotation number "2". At the same time, the information display device 20 increments the value of the counter box 118. The information display device 20 displays an attribute icon 106-2 near the highlighted mark 103a-2. While an attribute icon 106-1 is also displayed near the mark 103a-1 in the example illustrated in FIG. 6, the display or non-display of the attribute icons 106-1 and 106-2 is selectable, as described above. The annotation information also includes an annotation A1 including the mark 103a-1 and the attribute icon 106-1 and an annotation A2 including the mark 103a-2 and the attribute icon 106-2.

FIG. 7 is an enlarged view illustrating the annotation list 180. The information display device 20 updates the annotation list 180 as the annotation corresponding to the mark 103a-2 is added in the left-side area 201A of the screen. As illustrated in FIG. 7, a memo "normal spike" is added to the annotation number "2" in the annotation list 180.

Hereinafter, in the same manner, each time a certain portion or range on the signal waveforms is specified in the area 201A during the measurement, the specified portion is displayed with emphasis and annotation information is displayed along the time axis 112 in the display portion 110. The annotation information is sequentially added to the annotation list 180 in the area 201B.

The display of the annotation number is not indispensable and is not necessary to be used in the annotation list 180 and the area 201A displaying the signal waveforms. Any information that enables identification of an added annotation can be used as identification information. For example, an attribute icon and an attribute character string (for example, "strong spike") may be displayed in association with time near the time axis 112. Furthermore, a file number (number displayed in an item "File" in FIG. 6) may also be displayed in the area 201A.

If the end button 119 (illustrated in FIG. 4) in the left-side area 201A of the measurement and recording screen 205 is selected (pressed) and the measurement is finished, the information display device 20 stores the highlighted portion specified in the display portions 101 to 103 in association with the signal waveforms. The information display device 20 also stores the annotation information displayed on the corresponding time position in the display portion 110 in association with the annotation number and the time. The information display device 20 also stores related information including, for example, the counter value of the counter box 118 and content of the annotation list 180. The information display device 20 stores these pieces of display information to allow the analyst to easily recognize and analyze the questionable portion even if the analyst is different from the measurer.

Figure 8:
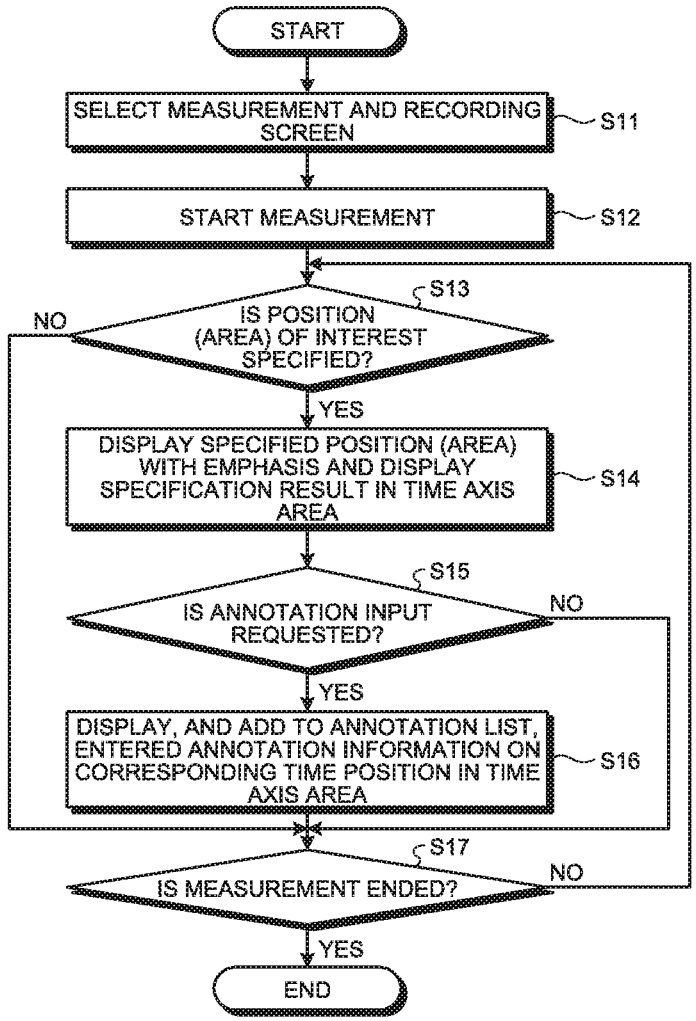
FIG. 8 is a flowchart schematically illustrating a flow of information display processing in a measurement and recording stage.

FIG. 8 is a flowchart schematically illustrating a flow of information display processing performed by the information display device 20 in the measurement and recording stage.

As illustrated in FIG. 8, after "Measurement and Recording" is selected on the start screen 204 illustrated in FIG. 2 (S11), the information display device 20 causes the measurement device 3 to start the measurement, and displays the waveforms of a plurality of signals in synchronization with each other along the same time axis (S12). The term "plurality of signal waveforms" includes both signal waveforms detected by a plurality of sensors of the same type and a plurality of signal waveforms detected by different types of respective sensors.

The information display device 20 subsequently determines whether a portion or range of interest has been specified on the displayed signal waveforms (S13).

If the portion or range of interest has been specified (Yes at S13), the information display device 20 displays the specified portion with emphasis in the display area (display portions 101 to 103) of the signal waveforms, and displays the specification result on a corresponding time position in the time axis area (display portion 110) (S14). The specification result includes information indicating the fact itself that the specification has been made or specified identification information.

Then, at the same time as, or before or after the display of the specification result in the time axis area, the information display device 20 determines whether a request for input of an annotation has been made (S15).

If the request, for input of an annotation has been made (Yes at S15), the information display device 20 displays entered annotation information on a corresponding time position in the time axis area, and adds the annotation information to the annotation list (S16).

The information display device 20 than determines whether a measurement end command has been entered (S17).

If no position (range) of interest has been specified (No at S13), or if no request for input of an annotation has been made (No at S15), the information display device 20 skips to Step S17 to determine whether to end the measurement. The information display device 20 repeats Steps S13 to S16 until the measurement ends (Yes at S17).

With this information display method, the measurement and recording screen 205 with high visibility of signal information is provided when the signals are collected from a plurality of sensors.

Operations During Analysis

The following describes operations during the analysis on the information display device 20.

Figure 9:
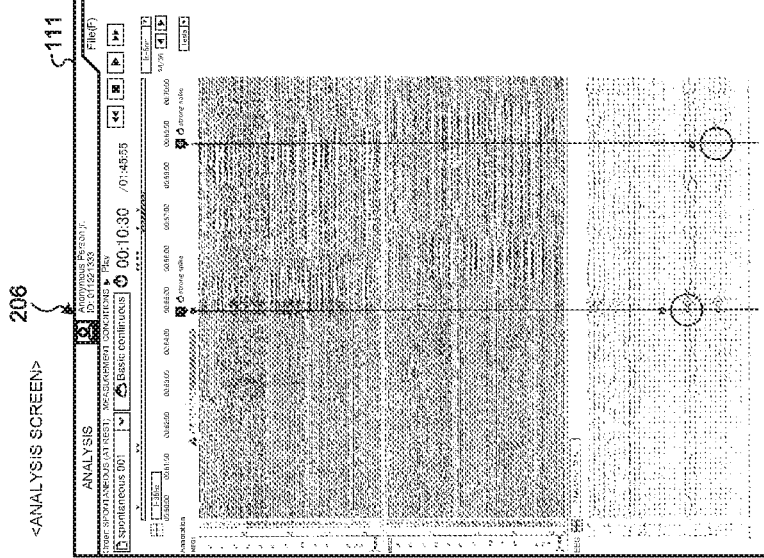
FIG. 9 is a front view illustrating an example of an analysis screen.

FIG. 9 is a front view illustrating an example of an analysis screen 206 displayed on the monitor display 26 of the information display device 20 during the analysis. As illustrated in FIG. 9, the analysis screen 206 is displayed by selecting an "Analysis" button on the start screen 204 of FIG. 2. The tab 111 on the screen displays that the analysis screen 206 is an "Analysis" screen. The analysis screen 206 includes an area 202A that displays the recorded signal waveforms together with the annotations and an area 202B that displays analysis information. The area 202A that displays the recorded signal waveforms and the annotation information is disposed on the left side of the screen as viewed from the measurer, and the area 202B that displays the analysis information is disposed on the right side as viewed from the measurer. This is because, during the analysis, efficient work is enabled to check or determine the analysis results in the area 202B using, for example, the mouse while checking or selecting the signal waveforms in the area 202A.

The analysis screen 206 displays the MEG signals in the second display portions 101 and 102 above a screen for the waveforms of the EEG signals in the second display portion 103 of the area 202A. In the area 202B on the right side of the area 202A of the analysis screen 206, the MEG distribution diagrams 141 and 142 are displayed on a side of the screen area that is closer to the area 202A and is in an upper portion of the screen, and the EEG distribution diagram 130 is displayed below the MEG distribution diagrams 141 and 142. As a result, the analyst can move the line of sight in the order from the "EEG signal waveforms" in the second display portion 103, to the "MEG signal waveforms" in the second display portions 101 and 102, to the MEG distribution diagrams 141 and 142, and to the EEG distribution diagram 130 (clockwise in this case). Therefore, the analyst (or the measurer) can efficiently move the line of sight, and as a result, the analysis work efficiency can be increased. The movement of the line of sight has been described above as clockwise, but is not limited to this example.

Figure 10:
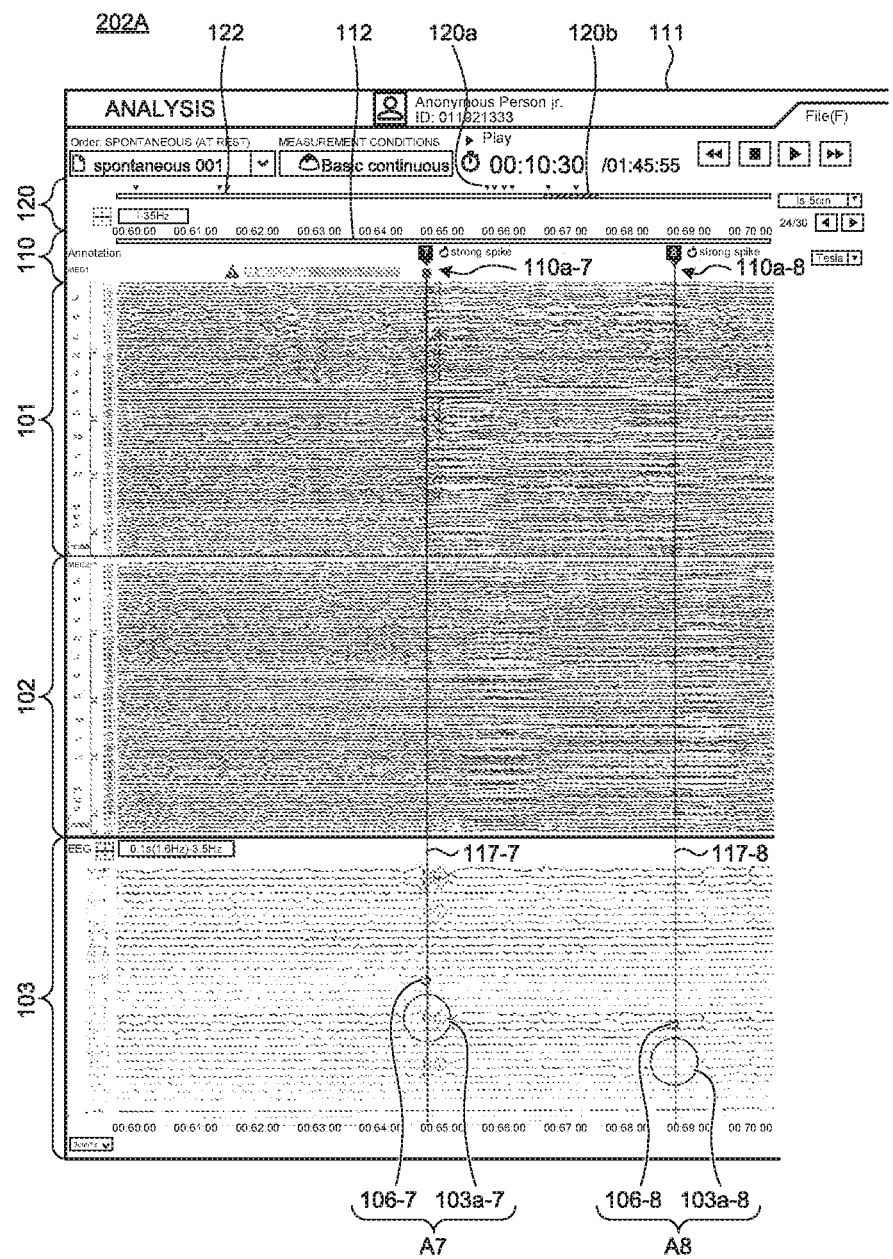
FIG. 10 is an enlarged view of a left-side area of the analysis screen.

FIG. 10 is an enlarged view of the left-side area 202A of the analysis screen 206. As illustrated in FIG. 10, the area 202A includes the display portion 110 and a display portion 120 that display time information during the measurement in the horizontal direction (first direction) of the screen and the display portions 101 to 103 that display recorded signal waveforms side by side in the vertical direction (second direction) of the screen for each type.

The information display device 20 displays the Lime axis 112 that indicates the lapse of time during the recording and annotations 110a-7 and 110a-8 added along the time axis 112 in the display portion 110. The information display device 20 displays a time axis 122 that indicates the total recording time in the display portion 120. The information display device 20 displays, along the time axis 122, pointer marks 120a that indicate time positions to which annotations have been added and a time zone 120b that indicates a time zone in which the signal waveforms currently displayed in the display portions 101 to 103 have been recorded. This display allows the analyst to intuitively understand in which stage of the measurement and recording a signal waveform currently being analyzed has been acquired.

After the analysis screen 205 is opened, the analyst can display the signal waveforms in a desired time zone in the display portions 101 to 103, for example, by dragging the time zone 120b on a bar of the time axis 122. Alternatively, as will be described later, the analyst can select a desired annotation from the annotation list 180 to display signal waveforms before and after those including the annotation in the display portions 101 to 103.

In the area 202A of the analysis screen 206 illustrated in FIG. 10, the display portions 101 to 103 display annotations A7 and A8 added to the signal waveforms during the recording. In the area 202A of the analysis screen 206 illustrated in FIG. 10, marks 103a-7 and. 103a-8 are highlighted, and corresponding attribute icons 106-7 and 106-8 are displayed near the marks 103a-7 and 103a-8. In the area 202A of the, analysis screen 206 illustrated in FIG. 10, vertical lines 117-7 and 117-8 indicating time positions of the marks 103a-7 and 103a-8 are displayed. Since the, line 117 is displayed, when, for example, an annotation is added in association with specification of a predetermined portion of the display portion 103, the result of the specification can also be easily viewed in the display portions 102 and 101 that are different types of signal display areas. The annotation information can include the line 117 in the sense of facilitating the viewing of the annotation information, and may be referred to as an "annotation line". Selecting the line 117 enlarges the display of the signal waveforms including a certain period of time before and after the time of the line 117. This processing will be described later.

Figure 11:
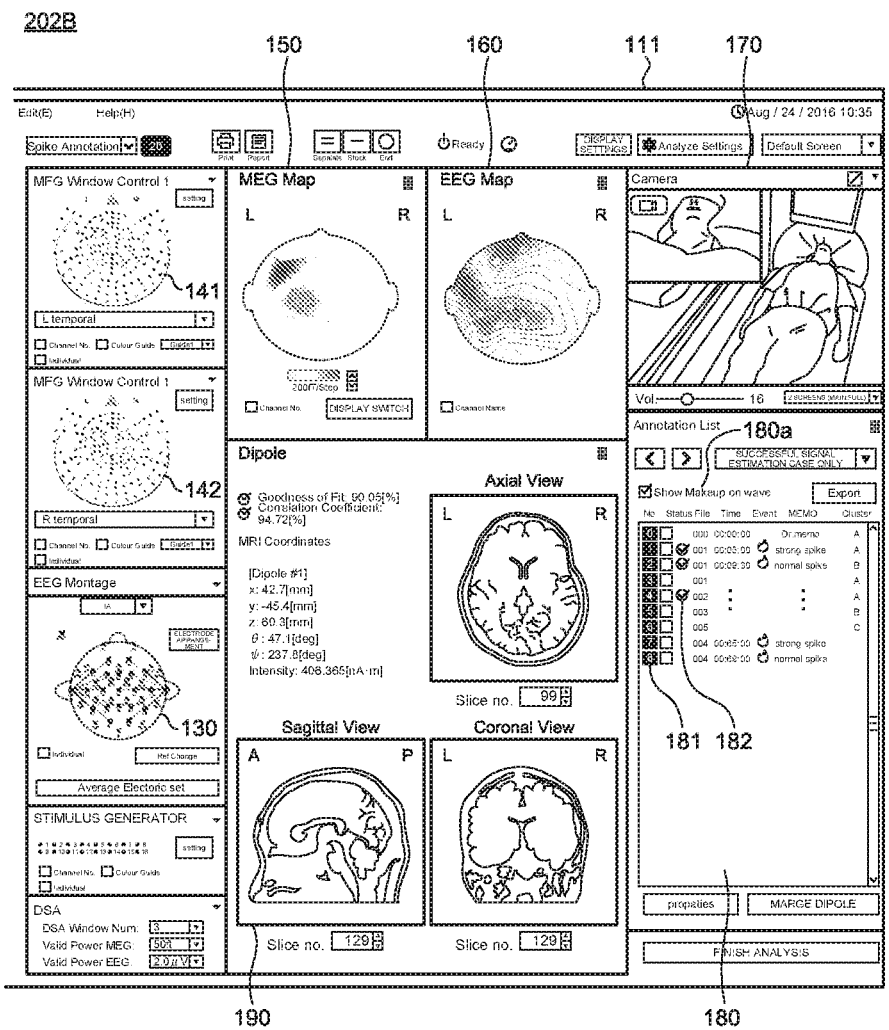
FIG. 11 is an enlarged view of a right-side area of the analysis screen.

FIG. 11 is an enlarged view of the right-side area 202B of the analysis screen 206, and illustrates a state at the same time as that of FIG. 10. The information display device 20 displays the MEG distribution diagrams 141 and 142 corresponding to the signal waveforms displayed in the display portions 101 and 102 of the area 202A and the EEG distribution diagram 130 corresponding to the signal waveforms displayed in the display portion 103 of the area 202A, in the area 202B of the analysis screen 206.

The information display device 20 displays an isomagnetic field map 150 of a magnetoencephalogram, a map area 160 of an electroencephalogram, and a display window 190 of tomographic images of the brain of the measurement subject acquired by magnetic resonance imaging (MRI), in the area 202B of the analysis screen 206. In the isomagnetic field map 150, a source region and a sink region of a magnetic field are displayed in a color-coded manner, and directions of current flow are visually perceived. The isomagnetic field map 150 and the map area 160 are information obtained after the completion of the measurement, and the tomographic images of the MRI is information separately obtained by an examination.

The video of the measurement subject while being measured is displayed on the monitor window 170 in synchronization with the time when the signal waveforms in the display portions 101 to 103 of the area 202A are acquired. The analyst can analyze the signal waveforms while checking the state of the measurement subject by watching the monitor window 170.

All the annotations added during the measurement and recording are listed in the annotation list 180. The annotation information (for example, attribute icons and text input information) added in association with annotation numbers 181 is listed in the annotation list 180. The annotation list 180 in the analysis screen 206 is displayed such that, for example, the, added annotations are arranged in ascending order (the oldest data is displayed at the top), but is not limited thereto. In the same manner as on the measurement and recording screen 205, the use of the annotation numbers is not indispensable. Each of the annotations can also be identified by a combination of time, a file name, an attribute, and the like. The display order of the annotations included in the annotation list 180 can be changed, and the list can be sorted for each item. A desired one of the annotation numbers 181 or the row thereof can be clicked to display the signal waveforms in a predetermined time zone including a time position to which the annotation has been added in the display portions 101 to 103 of the area 202A in FIG. 10.

On the analysis screen 206, unlike on the measurement and recording screen 205, the information display device 20 displays an estimation completion mark 182 (illustrated in FIG. 11) at an annotation for which the analyst has checked a signal waveform of the annotated part and finally estimated the signal source.

The information display device 20 disposes the display/ non-display selection box 180a for selecting the display or non-display of the annotations near the annotation list 180 in the area 202B of the analysis screen 206. If non-display is specified in the selection box 180a, the attribute icons 106-7 and 106-8 in the display portion 103 of FIG. 10 disappear. The non-display of the highlighted marks 103-7 and 103a-8 may be selectable by the display/non-display selection box 180a.

Figure 12:
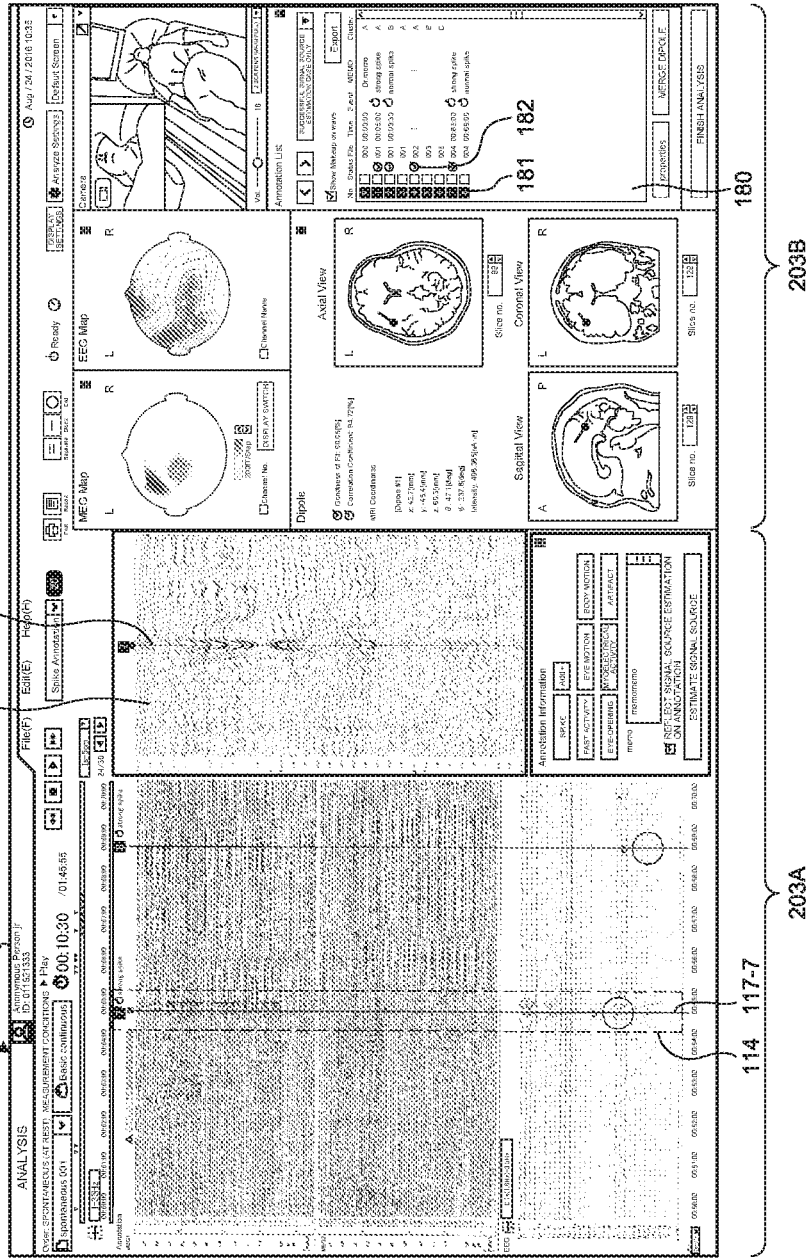
FIG. 12 is a front view of the analysis screen immediately after a line is selected.

FIG. 12 is a front view of the analysis screen 206 immediately after the line 117-7 is selected (for example, double-clicked). If the analyst focuses attention on the annotation A7 and selects (for example, double-clicks) the line 117-7 in order to analyze the waveforms in this area, the information display device 20 displays an enlarged view of signal waveforms near the highlighted signal waveforms in an enlargement display portion 200. The information display device 20 displays the enlarged view of the signal waveforms over a certain time range indicated by an area 114 together with a line 217-7 indicating the time position.

Figure 13:
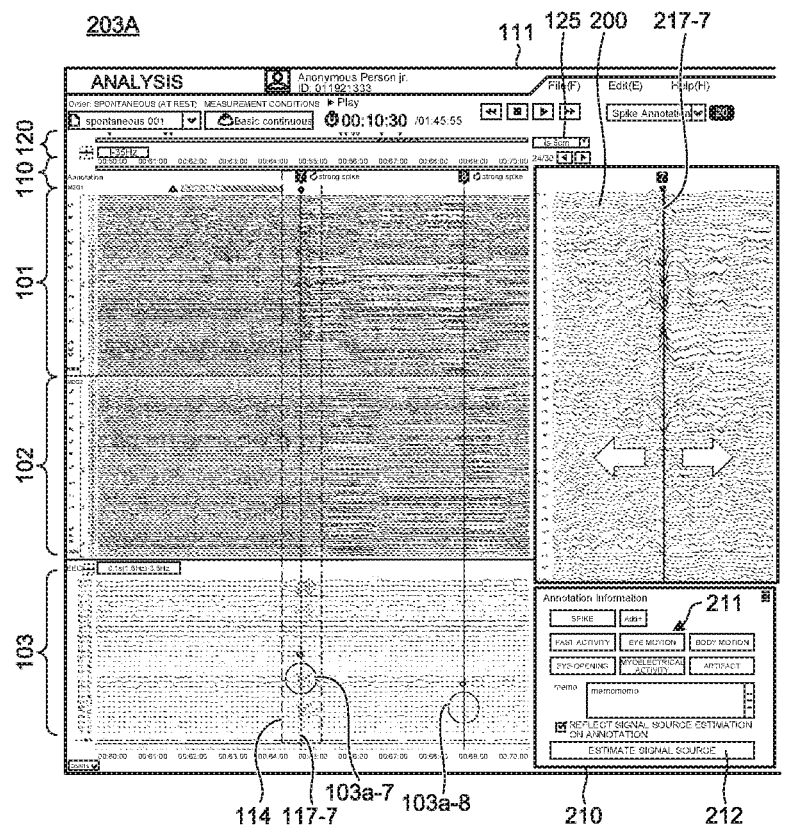
FIG. 13 is an enlarged view of a left-side area of the analysis screen illustrated in FIG. 12.

FIG. 13 is an enlarged view of a left-side area 203A (display area of signal waveforms) of the analysis screen 206 illustrated in FIG. 12. By displaying the enlarged view of the signal waveforms in the enlargement display portion 200 as illustrated in FIG. 13, the analyst can reconfirm validity of the mark added during the recording, or can check a waveform portion that has not been checked during the measurement and recording. For example, the analyst can specify or change the exact point of a questionable waveform by dragging the, line 217-7 to the right or left.

The information display device 20 may reflect a mark 103a or an attribute icon 106 or both displayed in a highlighted manner in the display portion 103 into the enlargement display portion 200. However, when the highlighted mark 103a or the highlighted attribute icon 106 (or both are) displayed in the enlargement display portion 200, the display thereof can be considered to hinder visibility at the time of accurate determination of singularity in amplitude. Therefore, the display or non-display thereof is preferably selectable.

The information display device 20 can also specify a type of the signal waveforms to be displayed in the enlargement display portion 200 and a channel range. For example, the analyst moves the line of sight from the mark 103a-7 highlighted in the display portion 103 to an upper portion of the screen, and checks whether singularity in amplitude is present in the signal waveforms in the display portion 101 or 102 of the MEG waveforms. In this case, the MEG waveforms associated with the mark 103a-7 can be displayed in an enlarged manner in the enlargement display portion 200 by entering a target channel region of the display portion 101 or 102 in a box 125.

As illustrated in FIG. 13, the information display device 20 displays a checking window 210 below the screen of the enlargement display portion 200. The checking window 210 includes attribute buttons 211 for the signal waveforms and a signal source estimation button 212. The attribute buttons 211 correspond to the attribute information included in the pop-up window 115 of the measurement and record screen 205, and, an attribute added during the recording is wrong, a correct attribute can be selected by selecting one of the attribute buttons 211. Once checking the correct position or attribute selection or both of the signal waveform, the analyst can reflect the estimation of the signal source to the annotation by clicking the estimation button 212.

Figure 14:
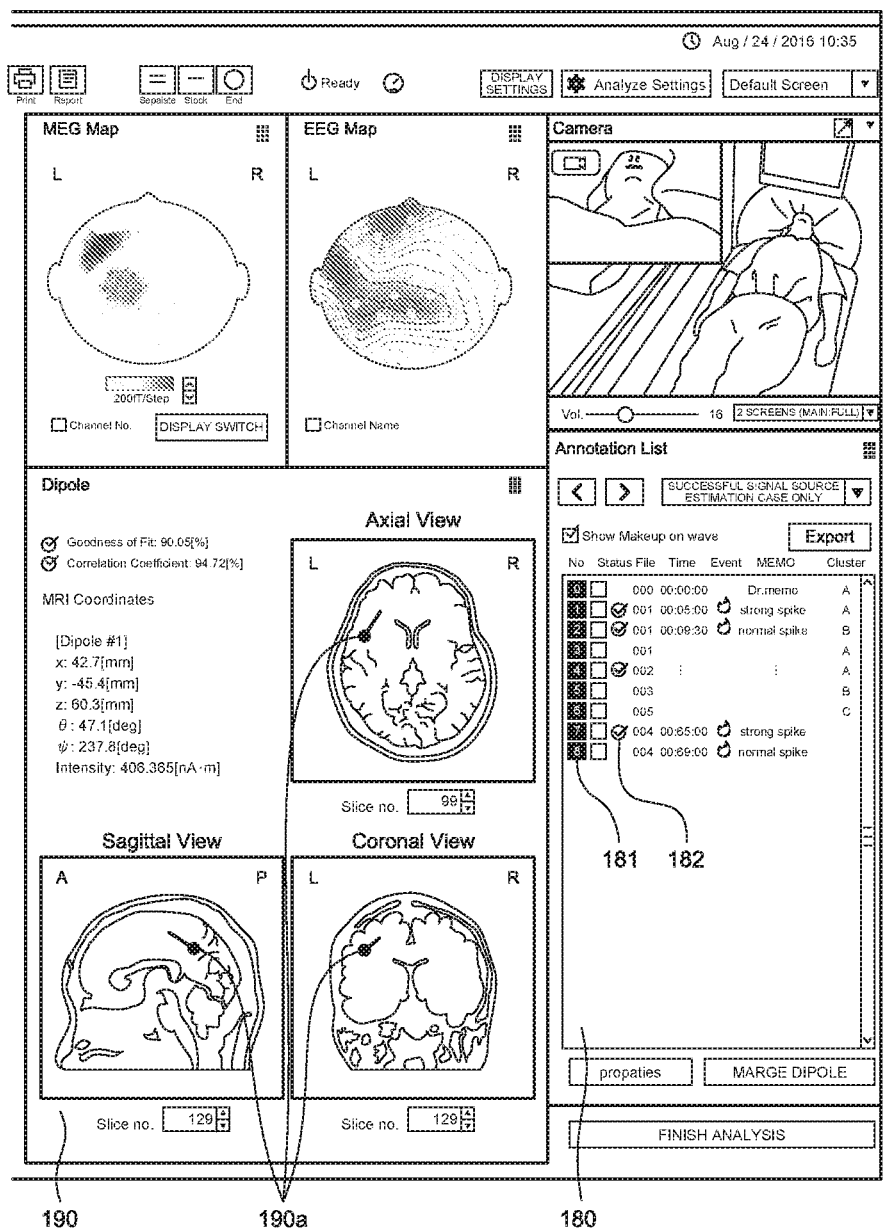
FIG. 14 is an enlarged view of a right-side area of the analysis screen illustrated in FIG. 12.

FIG. 4 is an enlarged view of a right-side area 203B of the analysis screen 206 illustrated in FIG. 12. In FIG. 13, after the position of the signal waveform or the attribute thereof is (or both are) checked for the desired annotation and the signal source estimation button 212 is selected, the information display device 20 adds the estimation completion mark 182 to the corresponding annotation this example, the annotation number "7") in the annotation list 180, as illustrated in FIG. 14. Furthermore, the information display device 20 displays an estimation result 190a of a dipole in the MRI tomographic image in the display window 190.

When the analyst changes the position of any of the marks highlighted in the display portions 101 to 103 or the content of any of the annotations 110a or both, two types of methods are available for updating the annotation list 180. One is a method of reflecting only the latest update information updated by the analyst into the annotation list 180, and the other is a method of adding the latest update information as new annotation information while keeping the annotation information at the time of the measurement and recording. If the latter method is employed, for example, a branch number from an annotation number at the time of the recording can be assigned as annotation identification information. In this case, the new annotation information may be added to the display portion 110, and the added annotation information may be displayed in a different color along the time axis.

Figure 15:
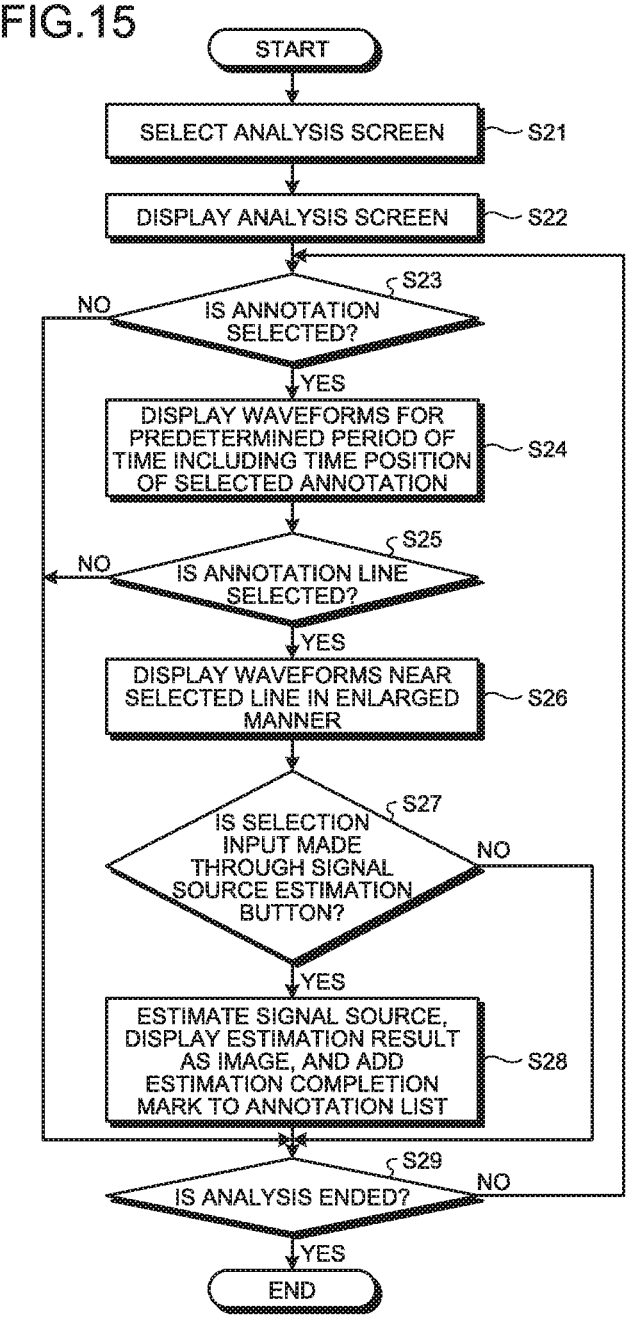
FIG. 15 is a flowchart schematically illustrating a flow of information display processing in an analysis stage.

FIG. 15 is a flowchart schematically illustrating a flow of information display processing performed by the information display device 20 in the analysis stage.

As illustrated in FIG. 15, after "Analysis" is selected on the start screen 204 (refer to FIG. 2) (S21), the information display device 20 starts the analysis, and displays the analysis screen 206 (S22). The initial analysis screen 206 may be a blank screen with no signal waveforms displayed thereon, or may be a screen with signal waveforms in a certain time range at the beginning or the end of the recording displayed thereon.

Then, after the analysis screen 206 is displayed, the information display device 20 determines whether a certain annotation has been selected (S23). The selection of the annotation nay be made by selecting a certain annotation number or a row in the annotation list 180, or may be made by specify a time position by manipulating the time zone 120b on the time axis 122 of the display portion 120.

If the annotation has been selected (Yes at S23), the information display device 20 displays a al wavelength for a predetermined period of time including the time position of the selected annotation (S24).

The information display device 20 subsequently determines whether the line 117 indicating the time position of the highlighted mark has been selected on the displayed scene (S25).

If the line 117 has been selected (Yes at S25), the information display device 20 displays the signal waveforms in a certain time range including the selected line in an enlarged manner (S26). The enlarged display is not limited to the signal waveforms near the highlighted mark, and different types of signal waveforms in the same time position may be displayed in an enlarged manner. For example, if an EEG signal waveform is marked with a highlighted mark, an MEG signal in the same time position may be displayed in an enlarged manner. Instead of displaying the signal waveform of all the channels in an enlarged manner, signal waveforms acquired in a certain range of channels including a channel from which a marked signal waveform has been acquired may be displayed in an enlarged manner. In this case, a determination may be made as to the type of a signal waveform to be displayed in an enlarged manner or as to whether the channel range has been specified, or as to both.

The information display device 20 subsequently determines whether the signal source estimation button 212 has been pressed (S27).

If a selection input through the signal source estimation button 212 has been made (Yes at S27), the information display device 20 proceeds to S23 to perform calculation of signal source estimation. Specifically, the information display device 20 displays the estimation result on an MRI tomographic screen, and adds the estimation completion mark 182 to the annotation list 180 (S28).

Thereafter, the information display device 20 determines whether an analysis end command has been entered (S29).

If no annotation has been selected (No at S23), if no annotation line for enlarged display has been selected (No at S25), or if the selection input through the signal source estimation button 212 has not been made (No at S27), the information display device 20 skips to Step S29 to determine whether to end the analysis. The information display device 20 repeats Steps S23 to S28 until the analysis end command is entered (Yes at S29).

The information display device 20 may determine whether an annotation has been changed between Steps S26 and S27. If an annotation has been changed, the information display device 20 reflects the change into the annotation list 180, and proceeds to the determination at Step S27.

The above-described display processing operations achieve the information display excellent in visibility and operability.

Figure 16:
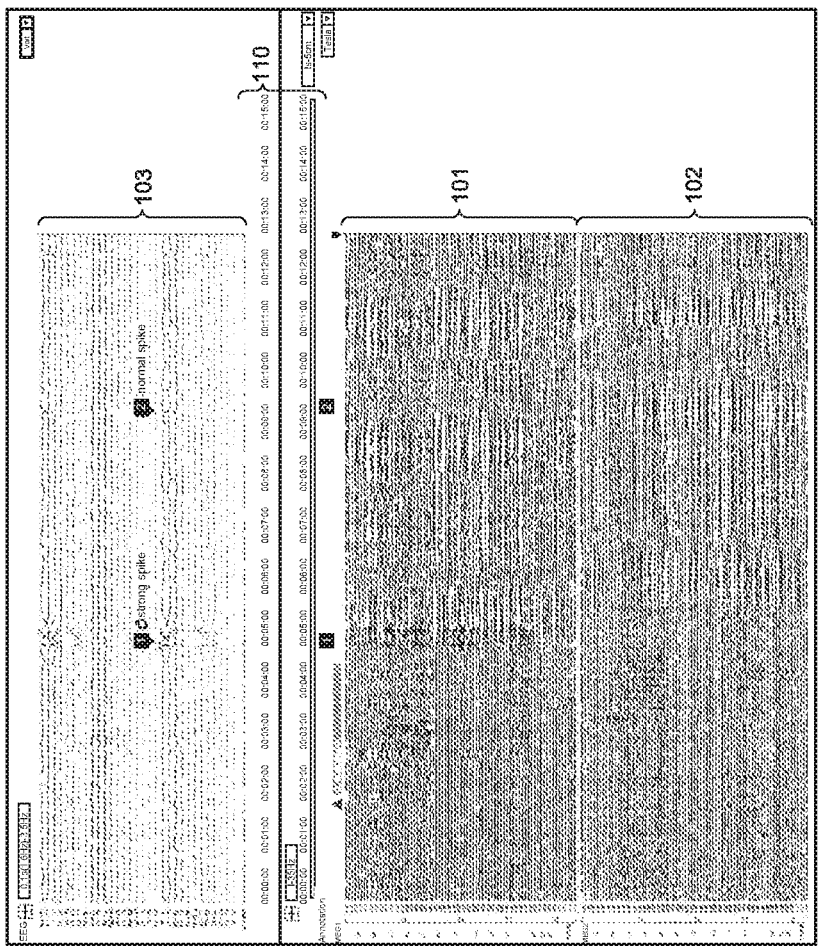
FIG. 16 is a view illustrating a modification of a display layout.
Figure 17:
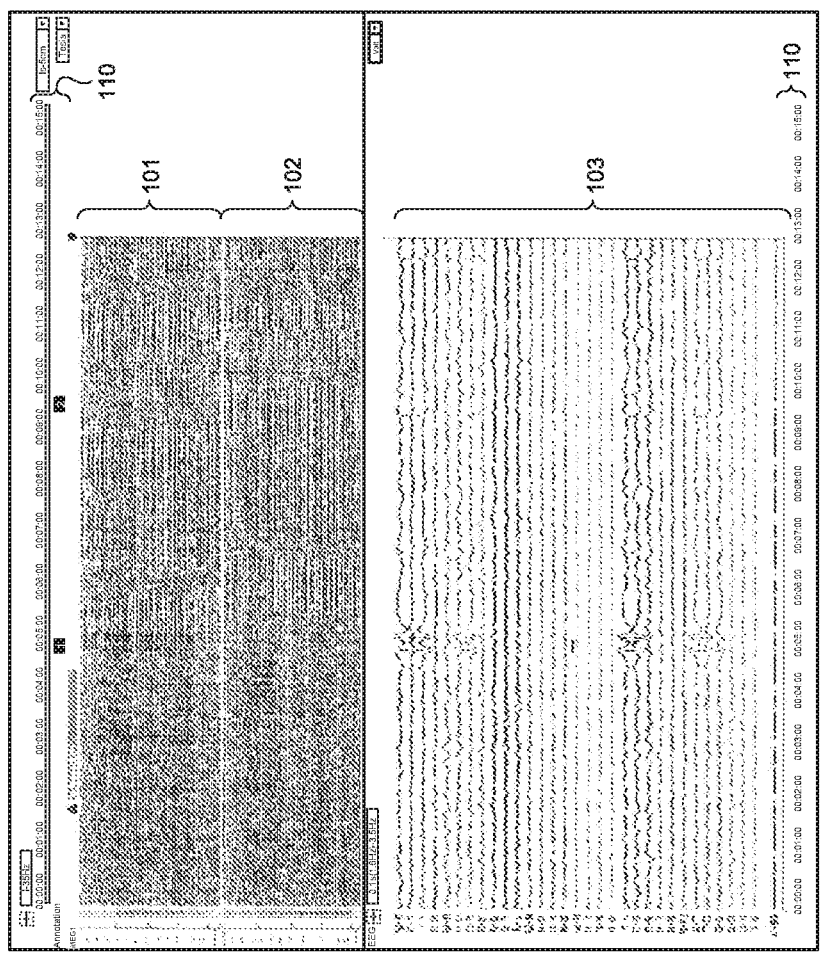
FIG. 17 is a view illustrating another modification of the display layout.

FIGS. 16 and 17 are views illustrating modifications of the display layout. When the signal waveforms acquired from a plurality of types of sensors are displayed, the information display device 20 can appropriately set the display positions according to the types of the sensors.

For example, as illustrated in FIG. 16, the information display device 20 may dispose the display portion 103 that displays the 63G signal waveforms that have large amplitudes and are easily visible in an upper portion of the screen. In this case, the MEG distribution diagrams 141 and 142 illustrated in FIG. 11 are disposed at the immediate right of the display portions 101 and 102, and the EEG distribution diagram 130 is disposed at the immediate right of the display portion 103 and above the MEG distribution diagrams 141 and 142.

As illustrated in FIG. 17, the information display device 20 may change the vertical size of a certain display portion. For example, the ratio in vertical size between the display portion 103 and the display portions 101 and 102 can be changed by selecting the frame of the display portion 103 for displaying the EEG waveforms and moving the frame in the up-down direction.

Furthermore, the information display device 20 may provide a position of the display portion 110 for displaying the timeline between the MEG waveforms and the EEG waveforms without limiting the position to the upper end or the lower end of the screen. The information display device 20 may also combine the timeline extend in the horizontal direction between the MEG waveforms and the EGG waveforms with the timeline or timelines disposed at the upper end or the lower end or both.

Noise Removal Process

The following describes noise removal processing of removing biologically dependent noise, such as a magnetic field that is generated from the heart and is mixed in the measured brain magnetic field signals. In the present embodiment, the noise removal processing at the time of the analysis will be described, but the noise removal processing is not limited thereto, and can be performed at the time of the measurement and recording without causing any problem. The biologically dependent noise is not limited to the magnetic field generated from the heart (magnetocardiographic noise), and includes a magnetic field caused by, for example, eye-blinking.

Figure 18:
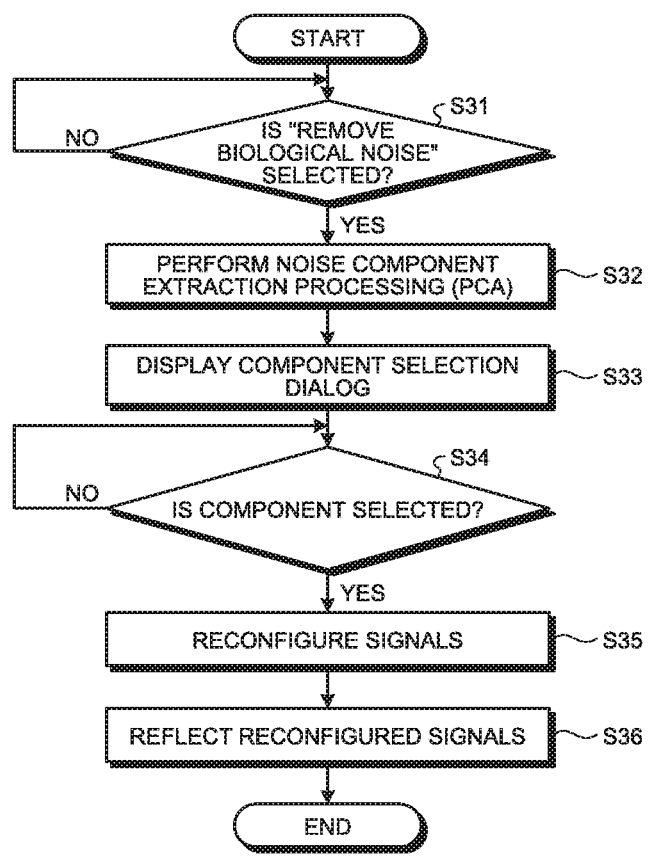
FIG. 18 is a flowchart schematically illustrating a flow of noise removal processing in the information display processing in the analysis stage.

FIG. 18 is a flowchart schematically illustrating a flow of the noise removal processing in the information display device 20 in the analysis stage. The analyst appropriately determines the timing of performing the noise removal processing. Specifically, the analyst may perform the noise removal processing if, immediately after the analysis screen 206 is displayed, the noise is determined to be mixed in the waveforms, or if the result obtained after the estimation of the signal source is unsatisfactory.

As illustrated in FIG. 18, the information display device 20 determines whether "Remove Biological Noise" has been selected from a menu on the analysis screen 206 (S31).

If "Remove Biological Noise" is determined to be selected from the menu on the analysis screen 206 (Yes at S31), the, information display device 20 (specific waveform display unit 251d, adjustment unit 251e, waveform display unit 251f, and sorting unit 251h (refer to FIG. 23)) performs component extraction processing (principal component analysis (PCA)) to extract intended components (components considered to be noise) from the signals (S32). The following describes in detail the component extraction processing (PCA).

The information display device 20 of the present embodiment uses the principal component analysis (PCA) as the component extraction processing. According to the principal component analysis (PCA), components representing the noise appear at higher levels when noise signals are appropriately extracted. In the present embodiment, the component extraction processing is performed using the principal component analysis (PCA), but is not limited thereto. The component extraction processing may be performed using independent component analysis (ICA).

Figure 19:
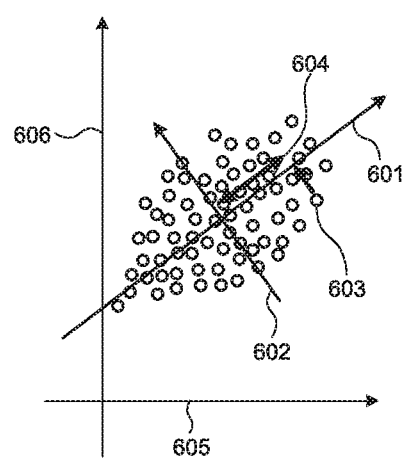
FIG. 19 is a diagram illustrating an example of a principal component analysis (PCA)

The following briefly describes the principal component analysis (PCA). FIG. 19 is a diagram, illustrating an example of the principal component analysis (PCA). In FIG. 19, reference numerals 605 and 606 denote the original axes, and axes 601 and 602 are axes (components) obtained by the principal component analysis (PCA). The principal component analysis (PCA) is a technique of transforming (rotating) the axes such that features of samples can be compared more easily than those of given samples. The samples can be more easily distinguished by projecting data of the given samples on the axis 601. The samples vary more widely as the data thereof is projected on the axis 602 obtained at a higher level.

As in the present embodiment, when a time duration before and after annotation time is extracted, samples that change from peak (valley) points to other points are entered into the principal component analysis (PCA). In other words, samples ranging from that including the highest noise to those including gradually decreasing noise are entered. Therefore, the variation among samples is larger when values of the samples are projected on the axis 601 representing the noise. In other words, the axis representing the noise component appears at a higher level.

Then, as illustrated in FIG. 18, after the component extraction processing (PCA) at S32 ends, the information display device 20 (noise component selection unit 251b (refer to FIG. 23)) displays a noise removal component selection dialog (S33), and receives a selection of an axis (component) representing the noise in the noise removal component selection dialog (S34). If the axis (component) representing the noise is selected in the noise removal component selection dialog (Yes at S34), the information display device 20 (reconfiguration unit 251c (refer to FIG. 23)) reconfigures the signals of all the channels based on the selection (S35).

The information display device 20 selects the axis (component) representing the noise from the results of the principal component analysis (PCA), removes components of the selected component to reconfigure the signals, and thus acquires signals without noise.

First, the following describes the selection of the axis (component) representing the noise from the results of the principal component analysis (PCA). A value obtained by projecting the data of the samples on a target component is called a score. In the case of the samples denoted as 603 in FIG. 19, the score of a first component (value projected on the first axis 601) is denoted as 604.

As described above, in the present embodiment, the PCA (principle component analysis) or the ICA (independent component analysis) is used to separate the superimposed noise signals.

However, in some cases, signals equivalent to the noise is difficult to be found from the decomposed components. Specifically, many components are extracted as results of the PCA or the ICA. For example, in the case of a system in which the number of sensors is 160, the signals are decomposed into 160 components. In that case, all the 160 components are difficult to be checked with human eyes to find the noise components. In particular, when the noise components appear at lower levels, the noise components are often left unchecked and overlooked. In other words, the results of the PCA or the ICA are generally often sorted in descending order of the contribution ratio (degree of influence on the original signals) and displayed. However, the contribution ratios of the noise components with higher contribution ratios are not always higher.

A method is available in which, to increase the contribution ratios of the noise components, a time zone in which the noise is generated is extracted and is subjected to the PCA or the ICA. For example, in the case of removing the noise caused by cardiac magnetism, about 10 to 20 noise generating points are specified, and the PCA or the ICA is applied to the vicinities thereof to increase the contribution ratios of the magnetocardiographic noise components. This operation can be automatically performed if, for example, an electrocardiograph is connected to the system. However, in other cases, it is troublesome to manually specify time of generation of the noise. Moreover in some cases, the same noise signal is separated into a plurality of components as a result of the PCA or the ICA. In these cases, although the components are desired to be removed as the noise, the components do not always appear in the vicinity when sorted based on the contribution ratio and it is difficult to remove all the corresponding components.

Accordingly, in the present embodiment, the sorting unit 251h (refer to FIG. 23) sorts the components in descending order of degree of periodicity thereof, and displays the sorted results. The sorting unit 251h uses the following method to sort the components.

Many of the noise components are periodical signals. For example, the power supplied and the cardiac magnetism are periodical signals. The noise components can be more easily identified by extracting the periodical signals from the components obtained by the PCA or the ICA and displaying the results as candidates for the noise components at the higher levels.

1. Method Using Autocorrelation

Autocorrelation is calculated for the components obtained by the PCA or the ICA. More in detail, data in a time zone appropriate for period lengths of assumed periodical noise components is extracted, and the autocorrelation of the data is calculated. For example, if the period of each of the assumed noise components is two seconds at the maximum, data for approximately four seconds is extracted and the autocorrelation of the data is calculated for a duration of two seconds.

The components are sorted in descending order from the maximum value in the positive direction of the autocorrelation, and displayed.

This method allows the components having higher periodicity to be displayed at higher levels, and thus can solve the problem that the contribution ratios of the noise components with higher contribution ratios are not always higher when the noise components are sorted in descending order of the contribution ratio (degree of influence on the original signals).

2. Method Using Cross-Correlation

Cross-correlation is calculated for the components obtained by the PCA or the ICA. The method for extracting the signals is the same as that described in Section 1 above.

Then, a cross-correlation matrix is calculated, and the maximum value of the cross-correlation is calculated. If the maximum value mentioned above is larger than a threshold $\alpha$ (for example, 0.8), components having a cross-correlation of the maximum value×$\beta$ (for example, 0.8) relative to two components having the above-mentioned maximum value are extracted and grouped.

The components having the above-described cross-correlation are displayed as the group. When the group is displayed, a component having the highest contribution ratio may be displayed as a representative, or the components in the group may be displayed side by side. The components included in the group are removed from the cross-correlation matrix, and the process returns to the processing of obtaining the maximum value through cross-correlation. This processing is continued until a condition is satisfied.

If the above-mentioned maximum value is smaller than the threshold $\alpha$, the remaining non-displayed components are displayed in descending order of the contribution ratio.

This method allows the components considered to be caused by the same noise to be collectively displayed at higher levels, and thus can solve the problem that it is difficult to remove all the corresponding components in the case where the same noise signal is separated into a plurality of components.

3. Method Using fast Fourier Transform (FFT)

A fast Fourier transform (FFT) is used to calculate the components obtained by the PCA or the ICA. More in detail, data in a time zone appropriate for assumed noise components is extracted, and the FFT thereof is used for calculation. For example, if the period of the assumed noise components is two seconds at the maximum, the data for four seconds is extracted and calculated by the FFT for a duration of two seconds.

The components are sorted in descending order of the maximum value in the positive direction of the FFT, and displayed.

This method allows the noise components to be displayed at higher levels, and thus can solve the problem that the contribution ratios of the noise components with higher contribution ratios are not always higher when the noise components are sorted in descending order of the contribution ratio (degree of influence on the original signals).

Figure 20:
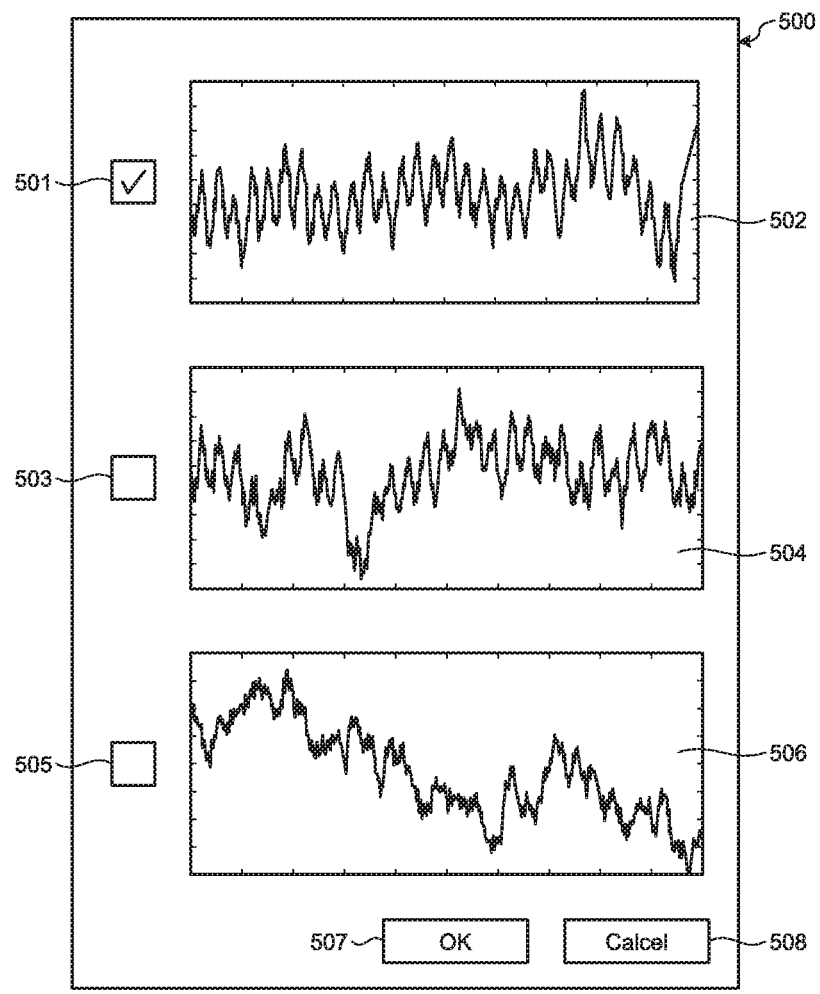
FIG. 20 is a front view illustrating an example of a noise removal component selection dialog.

FIG. 20 is a front view illustrating an example of a noise removal component selection dialog 500. As illustrated in FIG. 20, the noise removal component selection dialog 500 displayed on the monitor display 26 of the information display device 20 includes score display screens 502, 504, and 506 that display scores of first to third components in a manner sorted in descending order of the periodicity thereof. The noise removal component selection dialog 500 also includes check boxes 501, 503, and 505 associated with the score display screens 502, 504, and 506, respectively. Furthermore, the noise removal component selection dialog 500 includes an OK button 507 for determining a selection of a component and a cancel button 508 for canceling the selection of the component. The number of the displayed score display screens is not limited to three, and may be appropriately changeable by the analyst.

In the present embodiment, data in each time point serves as each sample. Accordingly, the score on the first component can be obtained by projecting the data in each time point on the first component. The obtained scores are displayed in accordance with the time points on the score display screens 502, 504, and 506.

Then, the following describes the reconfiguration of the signals of all the channels based on the selection at S34.

If the axis (component) representing the noise is selected and the OK button 507 is pressed on the noise removal component selection dialog 500, the information display device 20 reconfigures the signals. The information display device 20 (reconfiguration unit 251c) reconfigures the signals using scores of components other than the information on the component selected on the noise removal component selection dialog 500.

Figure 21:
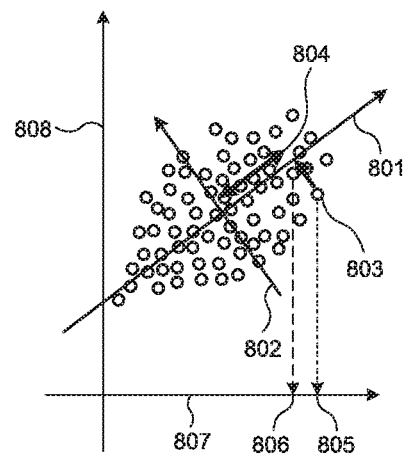
FIG. 21 is a diagram illustrating an example of a reconfiguration of signals according to the principal component analysis (PCA)

FIG. 21 is a diagram illustrating an example of the reconfiguration of the signals according to the principal component analysis (PCA). With reference to FIG. 21, a case will be described where the number of sensors (number of dimensions) is 2, for simplicity. In FIG. 21, reference numerals 807 and 808 denote the original axes, and axes 801 and 802 are axes (components) obtained by the principal component analysis (PCA). The information display device 20 reconfigures the value of a point, of a sample 803. The original value on the X-axis of the sample 803 is denoted as 805.

As illustrated in FIG. 21, the information display device 20 can calculate a score 804 (Score 1) by projecting the sample 803 on the axis 801 serving as Component 1. In the same manner, as illustrated in FIG. 21, the information display device 20 can also calculate a score 806 (Score 2) that has been projected on Component 2. The same coordinates of the sample 803 as the original can be represented by representing the sample 803 using both Score 1 and Score 2. The information display device 20 can calculate the original value 805 on the X-axis of the sample 803 as a value on the X-axis by projecting the coordinates of the sample 803 on the X-axis. In other words, the information display device 20 can reconfigure the same signals as the original ones by using the data of all the components.

Assume that Component 2 is specified, to the analyst, as a component representing the noise. In that case, Component 2 represents the noise components, and therefore is ignored when the reconfiguration is performed. In other words, a projection onto the axis 802 serving as Component 2 is ignored, and thus, the sample 803 is represented as the point 804 on Component 1. The information display device 20 obtains the point 806 obtained by projecting the point 804 on Component 1 onto the X-axis, as a signal reconfigured while ignoring the projection onto the axis 802 serving as the noise components, that is, as a signal obtained by removing the noise components.

Finally, as illustrated in FIG. 18, the information display device 20 reflects the signals of all the channels reconfigured at S35 (signals obtained by removing the noise) on the analysis screen 206 serving as a main page (S36), and ends the noise removal processing.

The reconfigured signals (signals obtained by removing the noise) displayed on the analysis screen 206 being the main page are used in processing in later stages including, for example, the dipole estimation.

The information display device 20 (reconfiguration unit 251c) may further present noise components based on the components representing the noise selected on the noise removal component selection dialog 500. This presentation allows the analyst to view, for example, only the magneto-cardiographic noise.

The following describes the information display device 20.

Figure 22:
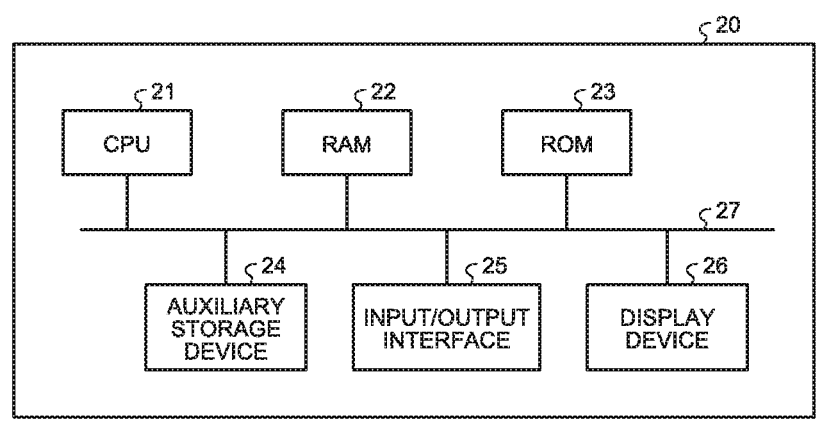
FIG. 22 is a hardware configuration diagram of an information display device.

FIG. 22 is a hardware configuration diagram of the information display device 20. The information display device 20 includes a central processing unit (CPU) 21, a random access memory (RAM) 22, a read-only memory (ROM) 23, an auxiliary storage device 24, an input/output interface 25, and a display device 26, which ace connected to each other through a bus 27.

The CPU 21 controls operations of the entire information display device 20, and performs various types of information processing. The CPU 21 also executes an information display program stored in the ROM 23 or the auxiliary storage device 24, and controls the display operations of the measurement and recording screen 205 and the analysis screen 206. The RAM 22 is used as a work area of the CPU 21, and may include a non-volatile RAM that stores therein main control parameters and information. The ROM 23 stores therein, for example, a basic input/output program. The ROM 23 may also store therein the information display program according to the present invention. The auxiliary storage device 24 is a storage device, such as a solid-state drive (SSD) or a hard disk drive (HDD), and stores therein, for example, a control program to control the operations of the information display device 20, various data required foe the operations of the information display device 20, and files. The input/output interface 25 includes both a user interface, such as a touchscreen panel, a keyboard, a display screen, and operation buttons, and a communication interface that acquires information from various sensors or the data recording server 42 and outputs the analysis information to other electronic devices. The display device 26 corresponds to the monitor display 26 of FIG. 1. The display device 26 displays the measurement and recording screen 205 and the analysis screen 206, and updates the screen thereof according to input/output operations via the input/output interface 25.

Figure 23:
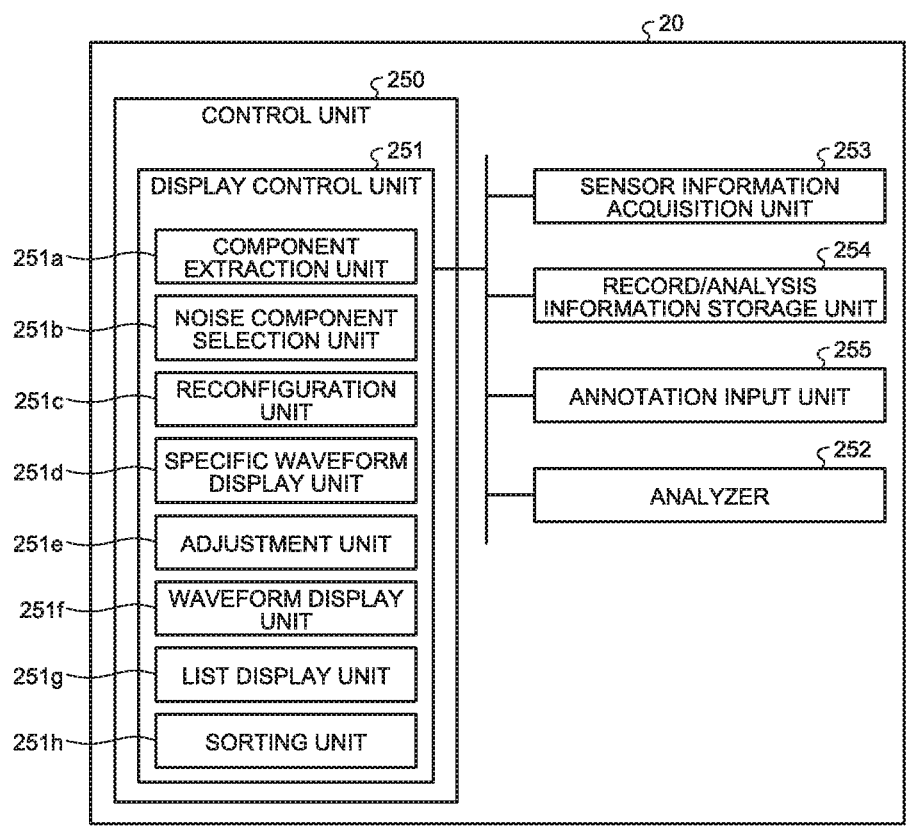
FIG. 23 is a functional block diagram of the information display device.

FIG. 23 is a functional block diagram of the information display device 20. The information display device 20 includes a control unit 250, an analyzer 252, a sensor information acquisition unit 253, a record/analysis information storage unit 254, and an annotation input unit 255. The control unit 250 includes a display control unit 251 that controls the screen display of the information display device 20.

The sensor information acquisition unit 253 acquires sensor information from the measurement device 3 or the data recording server 42. The annotation input unit 255 receives the annotation information added to the sensor information.

The analyzer 252 analyzes the collected sensor information. The analysis of the sensor information includes the analysis of the signal waveforms, analysis of the singularity in amplitude, and analysis of the brain magnetic field including the direction of the current dipole.

The display control unit 251 includes a component extraction unit 251a, the noise component selection unit 251b, the reconfiguration unit 251c, the specific waveform display unit 251d, the adjustment unit 251e, the waveform display unit 251f, a list display unit 251g, and the sorting unit 251h. The display control unit 251 controls the screen display during the measurement and recording and the analysis of the sensor information, using the methods described with reference to FIGS. 2 to 21.

The record/analysis information storage unit 254 stores the measured data and the analysis results. When an annotation has been added to a signal waveform during the measurement and recording, the annotation is also stored in association with the time information when the signal waveform was acquired.

The function of the control unit 250 including the display control unit 251 is implemented by the CPU 21 of FIG. 22. The function of the analyzer 252 is implemented by the CPU 21 and the RAM 22. The functions of the sensor information acquisition unit 253 and the annotation input unit 255 are implemented by the input/output inter ace 25. The function of the record/analysis information storage unit 254 is implemented by the ROM 23 or the auxiliary storage device 24.

When the operations of the information display device 20 of the embodiment ace performed by execution of the information display program, the information display program causes the CPU 21 to execute (a) a procedure to display the time axis of the signal detection in the first direction of the displayed first display portion screen, (b) a procedure to display a plurality of signal waveforms acquired in the signal measurement in parallel in the second direction different from the first direction in the displayed second display portions, and (c) a procedure in which, when a certain portion on at least one of the signal waveforms or in an area near the signal waveform is specified in any of the second display portions, the specified portion is displayed in a highlighted manner, and the result of the specification is also displayed as specification information on a time position in the first display portion corresponding to the specified portion.

When the operations of the information display device 20 of the embodiment are performed by execution of the information display program, the information display program causes the CPU 21 to execute a procedure to display a noise removal main dialog 300 and a procedure to display the noise removal component selection dialog 500, when the noise removal processing is performed.

When the above-described information display program is installed on the information display device 20, a position or range (area) of interest of a signal waveform can be easily viewed on the screen displaying a plurality of signal waveforms on the same time axis.

As described above, according to the present embodiment, desired components are extracted from a plurality of certain waveforms extracted from a plurality of signal waveforms based on the detected biological signals, and a selection with reference to display of the time of occurrence of the certain waveforms is received that selects one of the extracted results as a noise component. As a result, noise signals can be extracted without omission from complicated signals in which signals desired to be acquired and the noise signals are mixed without using an external device, and the process of noise removal can be verified to be optimal.

A user interface (UI) can be provided for the analyst to optimally extract, not as a different waveform obtained using an external device, noise waveforms from waveforms of a measured magnetic field.

The above-described embodiment has the configuration in which the measurement device 3 collects the EEG signals and the MEG signals, but the configuration is not limited thereto. For example, the measurement device 3 may collect the MEG signals, an electroencephalograph other than the measurement device 3 may collect the EEG signals, and the measurement device 3 and the electroencephalograph may output the respective biological signals to the data recording server 42.

An embodiment provides an effect that the noise components superimposed on the biological signals can be more easily detected.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information display device comprising:
   a component extraction unit configured to perform a principal component analysis or an independent component analysis to extract desired components from a plurality of signal waveforms based on detected biological signals;
   a sorting unit configured to sort a plurality of extracted results obtained by the component extraction unit in descending order of periodicity and display the sorted results; and
   a noise component selection unit configured to receive selection of one extracted result as a noise component from the extracted results obtained by the component extraction unit.

2. The information display device according to claim 1, further comprising a reconfiguration unit configured to remove the noise component based on the one extracted result received by the noise component selection unit, to reconfigure the signal waveforms.

3. The information display device according to claim 1, wherein the sorting unit is configured to sort the extracted results in descending order of heights of peaks of autocorrelation.

4. The information display device according to claim 1, wherein the sorting unit is configured to sort the extracted results in descending order of heights of peaks of a fast Fourier transform (FFT).

5. A biological signal measurement system: comprising:
   a measurement device configured to measure a measurement target to detect biological signals; and
   the information display device according to claim 1, the information display device being configured to receive the detected biological signals from the measurement device.

6. A computer program product comprising a non-transitory computer-readable medium including programmed instructions that cause a computer to function as:
   a component extraction unit configured to perform a principal component analysis or an independent component analysis to extract desired components from a plurality of signal waveforms based on detected biological signals;
   a sorting unit configured to sort a plurality of extracted results obtained by the component extraction unit in descending order of periodicity and display the sorted results; and
   a noise component selection unit configured to receive selection of one extracted result, as a noise component from the extracted results obtained by the component extraction unit.

* * * * *